US00PP21491P2

(12) United States Plant Patent
Koppe

(10) Patent No.: US PP21,491 P2
(45) Date of Patent: Nov. 16, 2010

(54) *BEGONIA* PLANT NAMED 'BETUKO'

(50) Latin Name: *Begonia×hiemalis*
Varietal Denomination: Betuko

(75) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 0 days.

(21) Appl. No.: 12/462,556

(22) Filed: Aug. 5, 2009

(51) Int. Cl.
*A01H 5/00* (2006.01)

(52) U.S. Cl. ..... Plt./347

(58) Field of Classification Search ..... Plt./347, Plt./344
See application file for complete search history.

(56) References Cited

OTHER PUBLICATIONS

Upov-rom GTITM Plant Variety Database 2010/03, GTI Jouve Retrieval Software, Citation for *Begonia* 'Betuko', one page.*

* cited by examiner

*Primary Examiner*—June Hwu
(74) *Attorney, Agent, or Firm*—C. A. Whealy

(57) ABSTRACT

A new and distinct cultivar of *Begonia* plant named 'Betuko', characterized by its upright, outwardly spreading and mounded plant habit; freely branching habit; dark green-colored leaves; semi-double flowers that are orange red in color and held above and beyond the foliage; and excellent postproduction longevity.

2 Drawing Sheets

Botanical designation: *Begonia×hiemalis.*
Cultivar denomination: 'Betuko'.

BACKGROUND OF THE INVENTION

The present invention relates to a new and distinct cultivar of *Begonia* plant, botanically known as *Begonia×hiemalis*, commercially known as Elatior Begonia and hereinafter referred to by the name 'Betuko'.

The new *Begonia* plant is a naturally-occurring whole plant mutation of *Begonia×hiemalis* 'Balemonk', not patented. The new *Begonia* plant was discovered and selected by the Inventor as a single flowering plant from within a population of plants of 'Balemonk' in a controlled greenhouse environment in Ermelo, The Netherlands in April, 2005.

Asexual reproduction of the new *Begonia* plant by vegetative cuttings taken in a controlled greenhouse environment in Ermelo, The Netherlands since June, 2006, has shown that the unique features of this new *Begonia* plant are stable and reproduced true to type in successive generations.

SUMMARY OF THE INVENTION

Plants of the new *Begonia* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Betuko'. These characteristics in combination distinguish 'Betuko' as a new and distinct *Begonia:*

1. Upright, outwardly spreading and mounded plant habit.
2. Freely branching habit.
3. Dark green-colored leaves.
4. Semi-double flowers that are orange red in color and held above and beyond the foliage.

5. Excellent postproduction longevity.

Plants of the new *Begonia* differ primarily from plants of the parent, 'Balemonk', in flower color as plants of 'Balemonk' have bright red-colored flowers. In addition, plants of the new *Begonia* have smaller flowers with fewer tepals per flower than plants of 'Balemonk'.

Plants of the new *Begonia* can be compared to plants of *Begonia×hiemalis* Berseba, not patented. In side-by-side comparisons conducted in Ermelo, The Netherlands, plants of the new *Begonia* differed primarily from plants of 'Berseba' in flower color as plants of 'Berseba' had red-colored flowers. In addition, plants of the new *Begonia* had slightly lighter green-colored leaves than plants of 'Berseba'.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'Betuko' grown in a container.

The photograph on the second sheet is a close up view of upper and lower surfaces of typical leaves of 'Betuko' (left) and upper, side and lower surfaces of typical flowers of 'Betuko' (right).

DETAILED BOTANICAL DESCRIPTION

The aforementioned photographs and following observations and measurements describe plants grown during the spring in Ermelo, The Netherlands, under commercial practice in a glass-covered greenhouse. During the production of the plants, the average day temperature was 20° C. and the average night temperature was 18° C. Plants were twelve weeks old when the photographs and description were taken. In the following description, color references are made to The Royal Horticultural Society Colour Chart, 2001 Edition, except where general terms of ordinary dictionary significance are used.

Botanical classification: *Begonia×hiemalis* 'Betuko'.

Commercial classification: Elatior Begonia.

Parentage: Naturally-occurring whole plant mutation of *Begonia×hiemalis* 'Balemonk', not patented.

Propagation:

*Type.*—By terminal vegetative cuttings.

*Time to develop roots.*—About 20 days at temperatures of 20° C.

*Time to produce a rooted young plant.*—About five weeks at temperatures of 20° C.

*Root description.*—Fine, fibrous; white/orange in color.

*Rooting habit.*—Freely branching; moderately dense; plants of the new *Begonia* have not been observed to form tubers.

Plant description:

*Plant form.*—Compact, upright and mounded plant habit, inverted triangle; freely branching with good stem and stem base strength; flowers are semi-double and positioned above the foliage.

*Growth habit.*—Vigorous growth habit; suitable for 11 to 14-cm containers; under optimal environmental and cultural conditions, usually about twelve weeks are required to produce proportional 12-cm potted plants from cuttings; vegetative shoots are formed at basal nodes and flowering shoots are formed at upper nodes.

*Plant height.*—About 20 cm to 25 cm.

*Plant width.*—About 30 cm to 35 cm.

*Leaves.*—Arrangement: Alternate; simple. Developing leaves, length: About 4 cm. Developing leaves, width: About 4.5 cm. Fully expanded leaves, length: About 12 cm. Fully expanded leaves, width: About 12.5 cm. Shape: Roughly reniform. Apex: Acute to broadly acute. Base: Cordate; asymmetric. Margin: Doubly serrate. Texture, upper and lower surfaces: Smooth, glabrous. Venation pattern: Palmate. Color: Developing leaves, upper surface: Close to N137A. Developing leaves, lower surface: Close to 147B. Fully expanded leaves, upper surface: Darker than 147A; venation, close to 147B. Fully expanded leaves, lower surface: Close to 191A; venation, close to 146B. Petioles: Length: About 1.5 cm to 7 cm. Texture, upper and lower surfaces: Slightly pubescent. Color, upper and lower surfaces: Close to 144C; with development, color becoming closer to 178B.

Flower description:

*Flowering habit.*—Semi-double flowers with tepals arranged in axillary cymes; usually five to seven flowers per cyme; numerous cymes in flower simultaneously; flowers positioned above and beyond the foliage; flowering continuous.

*Natural flowering season.*—Plants will flower year round regardless of nyctoperiod, however plants flower earlier and more abundantly from mid-February until November in the Northern Hemisphere.

*Flowers.*—Shape: Rounded; rose-like. Diameter: About 4 cm to 5 cm. Depth (height): About 2 cm.

*Flower buds.*—Length: About 8 mm to 16 mm. Diameter: About 2 mm to 3 mm. Color: Close to 39A.

*Tepals.*—Arrangement: Rosette. Quantity per flower: Usually about six to eight per flower. Size: Outer tepals, length: About 2.7 cm. Outer tepals, width: About 3 cm. Inner tepals, length: About 2 cm. Inner tepals, width: About 2.2 cm. Shape: Rounded flabellate. Apex: Rounded. Margin: Mostly entire to slightly crenate. Texture, upper and lower surfaces: Smooth, glabrous; satiny. Color: When opening, upper surface: Close to 33A. When opening, lower surface: Close to 39A to 39B. Fully opened, upper surface: Close to 33B. Fully opened, lower surface: Close to 39B.

*Flower bracts.*—Quantity/arrangement: Two, opposite. Shape: Broadly ovate. Apex: Acute. Margin: Slightly serrate. Texture, upper and lower surfaces: Glabrous, smooth. Color, upper and lower surfaces: Close to 146C partly overlain with close to 180A.

*Peduncles.*—Angle: Erect. Length: About 5 cm to 7 cm. Texture: Smooth, glabrous. Color: Close to 199A to 199B.

*Pedicels.*—Angle: Erect. Length: About 1.5 cm to 3 cm. Texture: Smooth, glabrous. Color: Close to 178C.

*Reproductive organs.*—Stamens: None observed. Pistils: None observed.

*Seed/fruit.*—Seed and fruit production have not been observed as reproductive organs are not formed.

Postproduction longevity:

*Individual flowers.*—Generally about two to three weeks.

*Whole plants.*—About six weeks under interior conditions.

Disease/pest resistance: Resistance to pathogens and pests common to *Begonia* has not been observed.

Temperature tolerance: Plants of the new *Begonia* have been observed to tolerate temperatures from about 10° C. to about 35° C.

It is claimed:

1. A new and distinct *Begonia* plant named 'Betuko' as illustrated and described.

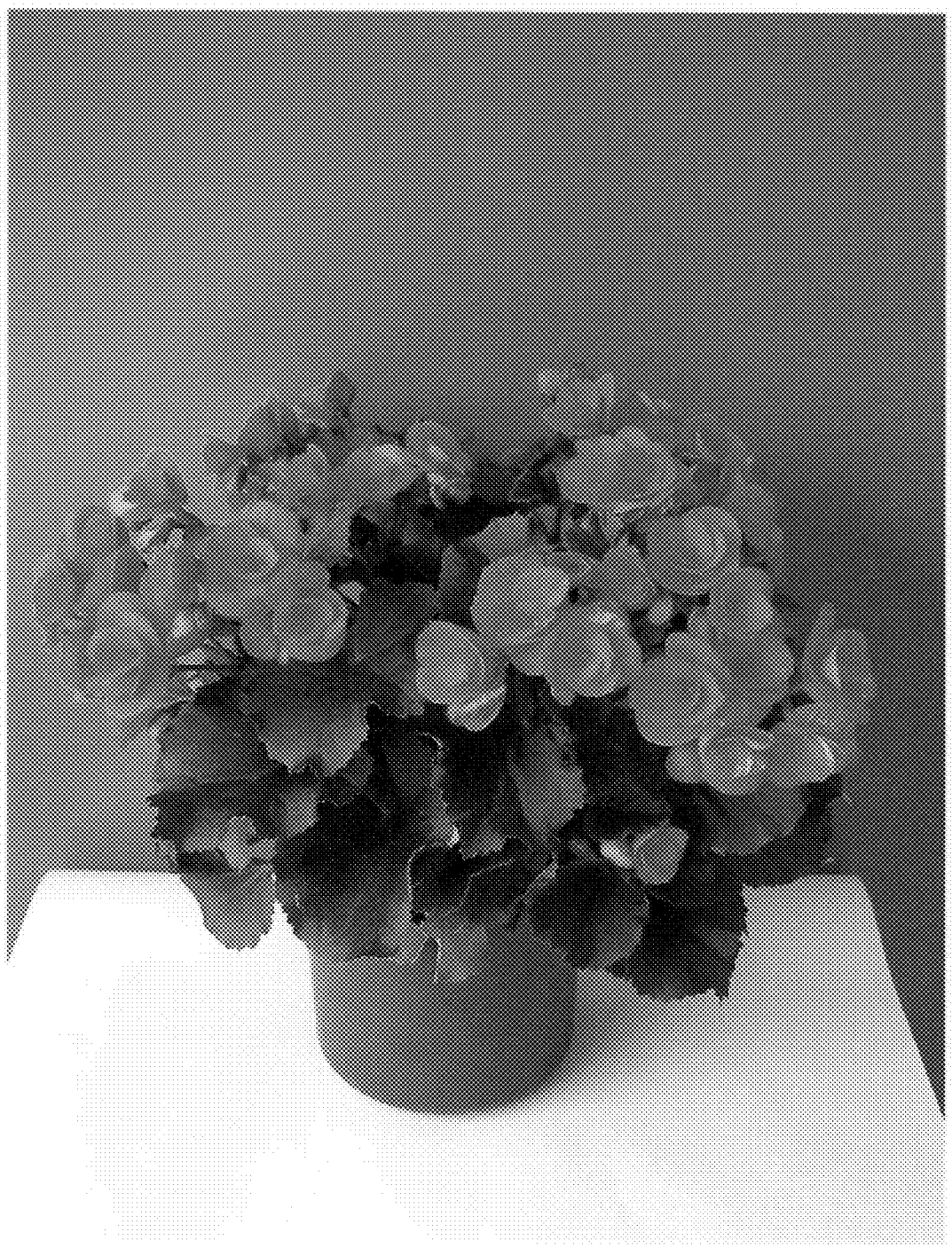

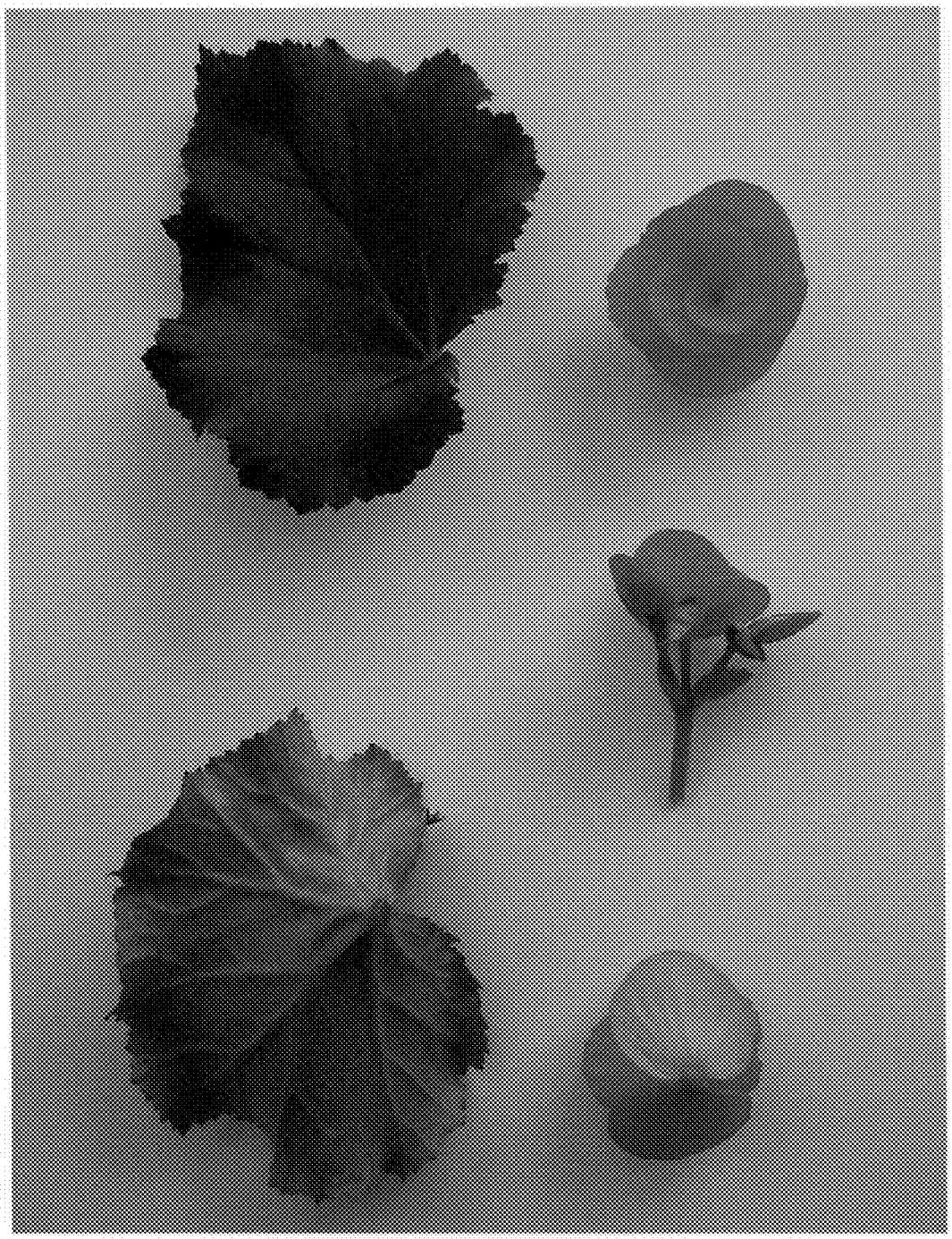

* * * * *